US00PP18493P2

(12) United States Plant Patent
Klemm

(10) Patent No.: US PP18,493 P2
(45) Date of Patent: Feb. 19, 2008

(54) ***DIASCIA* PLANT NAMED 'KLEDB05503'**

(50) Latin Name: *Diascia×hybrida*
Varietal Denomination: KLEDB05503

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/583,581

(22) Filed: Oct. 19, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Diascia* plant named 'KLEDB05503', characterized by its vigorous growth habit; freely flowering habit; and large dark orange-colored flowers.

1 Drawing Sheet

Botanical designation: *Diascia×hybrida.*
Cultivar denomination: 'KLEDB05503'.

BACKGROUND OF THE INVENTION

The present invention relates to a new and distinct cultivar of *Diascia,* botanically known as *Diascia×hybrida,* and hereinafter referred to by the name 'KLEDB05503'.

The new *Diascia* is a product of a planned breeding program conducted by the Inventor in Stuttgart, Germany. The objective of the breeding program is to create new compact *Diascia* cultivars with uniform plant habit and attractive flower colors.

The new *Diascia* originated from a cross-pollination made by the Inventor in Stuttgart, Germany in June, 2003 of a proprietary selection of *Diascia×hybrida* identified as code number GW 002, not patented, as the female, or seed, parent with a proprietary selection of *Diascia×hybrida* identified as code number GW 001, not patented, as the male, or pollen, parent. The cultivar KLEDB05503 was discovered and selected by the Inventor as a flowering plant within the progeny of the stated cross-pollination in a controlled environment in Stuttgart, Germany in June, 2004.

Asexual reproduction of the new *Diascia* by terminal cuttings in a controlled environment in Stuttgart, Germany since September, 2004, has shown that the unique features of this new *Diascia* are stable and reproduced true to type in successive generations.

SUMMARY OF THE INVENTION

The cultivar KLEDB05503 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEDB05503'. These characteristics in combination distinguish 'KLEDB05503' as a new and distinct cultivar of *Diascia:*

1. Vigorous growth habit.
2. Freely flowering habit.
3. Large dark orange-colored flowers.

Plants of the new *Diascia* can be compared to plants of the female parent selection. Plants of the new *Diascia* differ from plants of the female parent selection in the following characteristics:

1. Plants of the new *Diascia* have larger flowers than plants of the female parent selection.
2. Plants of the new *Diascia* and the female parent selection differ in flower color as plants of the female parent selection have white-colored flowers.

Plants of the new *Diascia* can be compared to plants of the male parent selection. Plants of the new *Diascia* differ primarily from plants of the male parent selection in growth habit as plants of the new *Diascia* are more vigorous than plants of the male parent selection.

Plants of the new *Diascia* can be compared to plants of the *Diascia×hybrida* cultivar Red Ace, disclosed in U.S. Plant patent application Ser. No. 09/639,898, now abandoned. In side-by-side comparisons conducted in Stuttgart, Germany, plants of the new *Diascia* differed from plants of the cultivar Red Ace in the following characteristics:

1. Plants of the new *Diascia* had larger flowers than plants of the cultivar Red Ace.
2. Flowers of plants of the new *Diascia* and the cultivar Red Ace differed in flower color as plants of the cultivar Red Ace had red-colored flowers.

BRIEF DESCRIPTION OF THE PHOTOGRAPH

The accompanying colored photograph illustrates the overall appearance of the new *Diascia,* showing the colors as true as it is reasonably possible to obtain in colored reproductions of this type. Colors in the photograph may differ slightly from the color values cited in the detailed botanical description which accurately describe the colors of the new *Diascia.* The photograph comprises a close-up view of a typical flowering plant of 'KLEDB05503' grown in a container.

DETAILED BOTANICAL DESCRIPTION

The photograph and following observations, measurements and values describe plants grown in Stuttgart, Germany in 11-cm containers in a glass-covered greenhouse during the spring and under conditions which closely approximate commercial production. During the production of the plants, day temperatures ranged from 18° C. to 22° C., night temperatures ranged from 12° C. to 18° C. and maximum light levels were 60,000 lux. Plants were pinched one time and were about eleven weeks old when the photograph and the description were taken. In the description, color references are made to The Royal Horticultural Society Colour Chart, 1995 Edition, except where general terms of ordinary dictionary significance are used.

Botanical classification: *Diascia×hybrida* cultivar KLEDB05503.

Parentage:

*Female, or seed, parent.*—Proprietary selection of *Diascia×hybrida* identified as code number GW 002, not patented.

*Male or pollen parent.*—Proprietary selection of *Diascia×hybrida* identified as code number GW 001, not patented.

Propagation:

*Type.*—By terminal vegetative cuttings.

*Time to initiate roots, summer.*—About five days at temperatures of 25° C.

*Time to initiate roots, winter.*—About eight days at temperatures of 25° C.

*Time to develop roots, summer.*—About ten days at temperatures of 25° C.

*Time to develop roots, winter.*—About 14 days at temperatures of 25° C.

*Root description.*—Fine, fibrous; pale white in color.

*Rooting habit.*—Freely branching; dense.

Plant description:

*Plant form and growth habit.*—Compact, upright and somewhat outwardly spreading plant habit. Vigorous growth habit.

*Branching habit.*—Freely branching, about 17 lateral branches develop per plant; pinching enhances branching.

*Plant height.*—About 15 cm to 17 cm.

*Plant diameter* (*area of spread*).—About 22 cm to 24 cm.

Lateral branch description:

*Length.*—About 17 cm.

*Diameter.*—About 3 mm.

*Internode length.*—About 1.3 cm.

*Texture.*—Smooth, glabrous.

*Color.*—146B.

Foliage description:

*Arrangement.*—Alternate, simple.

*Length.*—About 2 cm.

*Width.*—About 1.1 cm.

*Shape.*—Lanceolate.

*Apex.*—Cuspidate.

*Base.*—Cordate.

*Margin.*—Serrate.

*Texture, upper and lower surfaces.*—Smooth, glabrous.

*Venation pattern.*—Pinnate; arcuate.

*Color.*—Developing and fully expanded foliage, upper surface: 147A; venation, 147A. Developing and fully expanded foliage, lower surface: 147B; venation, 147B.

*Petiole.*—Length: About 1 mm. Diameter: About 1 mm. Texture, upper and lower surfaces: Smooth, glabrous. Color, upper and lower surfaces: 146C.

Flower description:

*Flower arrangement.*—Single flowers arranged on terminal racemes. Freely flowering habit with usually about 22 open flowers and flower buds per lateral branch. Flowers face outwardly. Flowers not fragrant.

*Natural flowering season.*—Plants flower continuously from May through September in Germany. Flowers last about five days on the plant. Flowers not persistent.

*Inflorescence height.*—About 3 cm.

*Inflorescence width.*—About 2 cm.

*Flower diameter.*—About 2 cm.

*Flower length* (*height*).—About 5 mm.

*Flower bud.*—Length: About 2 mm. Diameter: About 3 mm. Shape: Rounded. Color: 144D.

*Petals.*—Arrangement: Corolla consists of five petals modified into two banner petals, two lateral petals with spurs and a protruding lip petal. Length: About 1 cm. Width: About 1 cm. Shape: Obovate. Apex: Rounded. Base: Attenuate. Margin: Entire. Texture, upper and lower surfaces: Smooth, glabrous, satiny. Color: When opening, upper surface: 32A. When opening, lower surface: 32B. Fully opened, upper surface: 33A; throat, close to 59A. Fully opened, lower surface: 32A; nectar spurs, 59A.

*Sepals.*—Appearance: Five sepals fused into a star-shaped calyx. Length: About 2 mm. Width: About 1 mm. Shape: Lanceolate. Apex: Cuspidate. Margin: Entire. Texture, upper and lower surfaces: Smooth, glabrous. Color, upper surface: 138A. Color, lower surface: 137B.

*Peduncles.*—Length: About 4 cm. Diameter: About 2 mm. Angle: Erect. Strength: Strong. Texture: Smooth. Color: 137C.

*Pedicels.*—Length: About 1 cm. Diameter: About 1 mm. Angle: Erect. Strength: Moderately strong. Texture: Smooth. Color: 146B.

*Reproductive organs.*—Androecium: Stamen number: About four. Anther shape: Ovate. Anther length: About 1 mm. Anther color: 46A. Amount of pollen: Moderate. Pollen color: 13A. Gynoecium: Pistil length: About 1 mm. Style length: About 1 mm. Style color: 146D. Stigma appearance: Rounded. Stigma color: 151B. Ovary color: 144A.

*Seeds.*—Length: About 1 mm. Diameter: About 1 mm. Color: 177A.

Temperature tolerance: Plants of the new *Diascia* have been observed to tolerate temperatures from about 1° C. to about 35° C.

Pathogen/pest resistance: Plants of the new *Diascia* have not been shown to be resistant to pathogens and pests common to *Diascia*.

It is claimed:

1. A new and distinct *Diascia* plant named 'KLEDB05503' as illustrated and described.

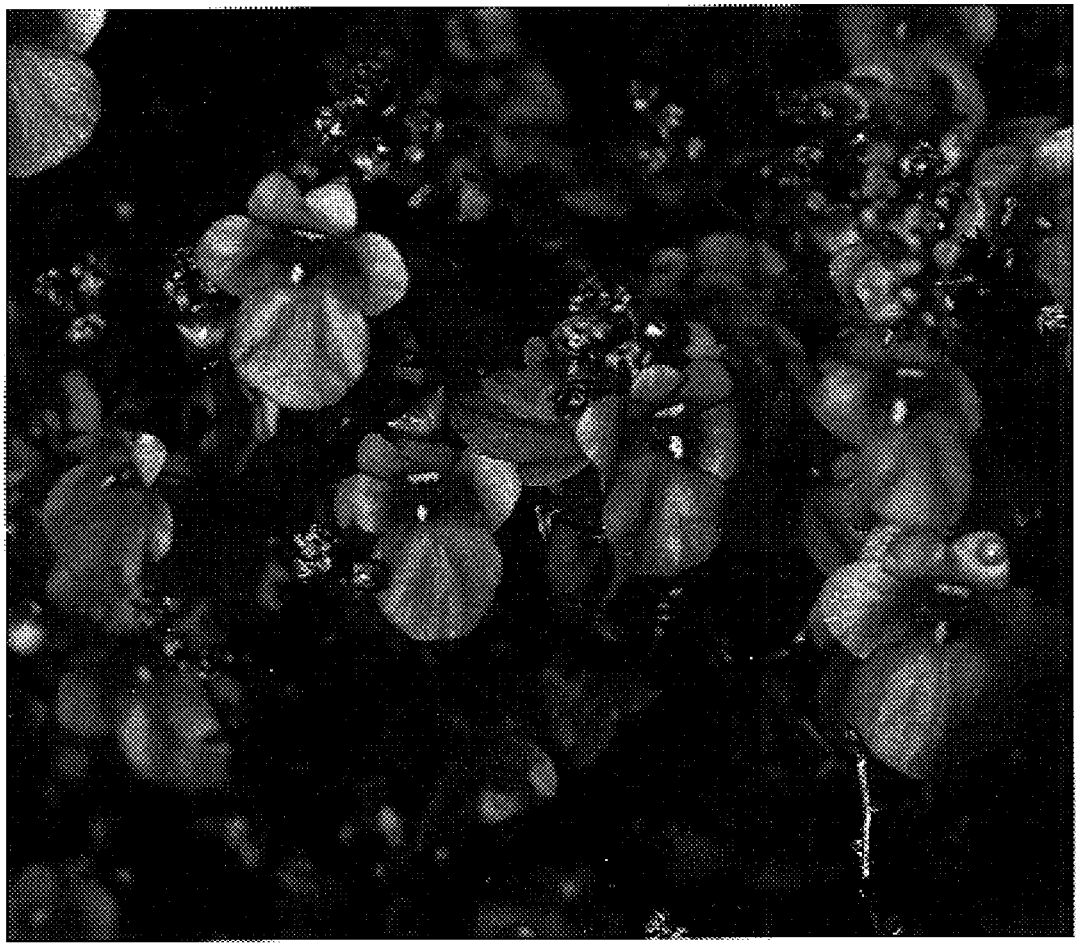

* * * * *